(12) United States Patent
Lee et al.

(10) Patent No.: US 12,097,272 B2
(45) Date of Patent: Sep. 24, 2024

(54) ULTRAVIOLET PROTECTION PATCH AND APPLICATION METHOD THEREOF

(71) Applicant: AMOLIFESCIENCE CO., LTD., Seoul (KR)

(72) Inventors: Su Yeon Lee, Gimpo-si (KR); Ji Young Kim, Gimpo-si (KR); Hyo Jung Lee, Seoul (KR); In Yong Seo, Seoul (KR); Seoung Hoon Lee, Paju-si (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 742 days.

(21) Appl. No.: 17/292,176

(22) PCT Filed: Nov. 8, 2019

(86) PCT No.: PCT/KR2019/015139
§ 371 (c)(1),
(2) Date: May 7, 2021

(87) PCT Pub. No.: WO2020/096404
PCT Pub. Date: May 14, 2020

(65) Prior Publication Data
US 2021/0386630 A1    Dec. 16, 2021

(30) Foreign Application Priority Data

Nov. 8, 2018  (KR) .......................... 10-2018-0136657
Nov. 27, 2018  (KR) .......................... 10-2018-0148160

(51) Int. Cl.
*A61K 8/35*    (2006.01)
*A61K 8/02*    (2006.01)
(Continued)

(52) U.S. Cl.
CPC .............. *A61K 8/0208* (2013.01); *A61K 8/35* (2013.01); *A61K 8/40* (2013.01); *A61K 8/87* (2013.01)

(58) Field of Classification Search
CPC ........................................................ A61K 8/35
See application file for complete search history.

(56) References Cited

U.S. PATENT DOCUMENTS 10,470,983 B2    11/2019  Seo et al.
2020/0086099 A1    3/2020  Seo et al.

FOREIGN PATENT DOCUMENTS

JP    3171286 U    10/2011
KR    101047931 B1    7/2011
(Continued)

OTHER PUBLICATIONS

International Search Report cited in PCT/KR2019/015139 dated Feb. 25, 2020, 2 pages.

*Primary Examiner* — Benjamin J Packard
(74) *Attorney, Agent, or Firm* — Rothwell, Figg, Ernst & Manbeck, P.C.

(57) ABSTRACT

An ultraviolet protection patch is provided. An ultraviolet protection patch, according to one embodiment of the present invention, is implemented by comprising: an ultraviolet protection layer including a support component and an ultraviolet protection agent; and a first shape-retaining layer which is a fiber web provided on one surface of the ultraviolet protection layer. According to this, as the ultraviolet protection patch comprises the ultraviolet protection layer and the shape-retaining layer which have predetermined properties, an ultraviolet protection material does not directly contact the skin, and thus skin trouble, irritation, and white cast do not occur, and as the patch is excellent in elasticity, the patch has excellent stiffness without inhibiting movement of a site to which the patch is adhered or peeling (Continued)

off even by physical stimuli, and the ultraviolet protection layer and the shape-retaining layer have a predetermined basis weight relationship, thereby having excellent transparency, and thus, there is an effect of not reducing visibility of the site to which the patch is adhered when the patch is adhered to the skin.

12 Claims, 3 Drawing Sheets

(51) Int. Cl.
  *A61K 8/40* (2006.01)
  *A61K 8/87* (2006.01)

(56) References Cited

FOREIGN PATENT DOCUMENTS

| | | |
|---|---|---|
| KR | 20110077792 A | 7/2011 |
| KR | 20110137157 A | 12/2011 |
| KR | 20170024544 A | 3/2017 |
| KR | 20180067177 A | 6/2018 |
| WO | 2013066022 A1 | 5/2013 |

ULTRAVIOLET PROTECTION PATCH AND APPLICATION METHOD THEREOF

CROSS REFERENCE TO RELATED APPLICATION

This application is a 35 U.S.C. 371 National Phase Entry Application from PCT/KR2019/015139, filed Nov. 8, 2019, which claims the benefit of Korean Patent Application Nos. 10-2018-0136657 filed Nov. 8, 2018 and 10-2018-0148160 filed on Nov. 27, 2018, the disclosures of which are incorporated herein in their entirety by reference.

TECHNICAL FIELD

The present invention relates to an ultraviolet protection patch, and more particularly, to an ultraviolet protection patch and a method of applying the same.

BACKGROUND ART

Ultraviolet rays from sunlight are a major cause of skin erythema, edema, freckles, or skin cancer. Recently, a great deal of research has been actively conducted on various skin diseases caused by ultraviolet rays.

Generally, ultraviolet rays may refer to light having a wavelength of 200 nm to 400 nm and may be classified into ultraviolet A (320 nm to 400 nm), ultraviolet B (280 nm to 320 nm), and ultraviolet C (100 nm to 280 nm) according to wavelengths. Among the ultraviolet rays, ultraviolet C has strong energy but is mostly absorbed and removed by the ozone layer present in the Earth's stratosphere and thus usually has little influence on living things. However, it is known that ultraviolet B penetrates into the epidermis of skin to cause erythema, freckles, edema, or the like. In addition, it is known that ultraviolet A penetrates into the derma of skin to cause skin aging and skin irritation, thereby stimulating skin cancer, wrinkles, and melamine formation. Furthermore, a great deal of epidemiologic research has also proven that there is a relationship between sun exposure and human skin cancer.

As the public interest in protecting skin from such ultraviolet rays is increased, the importance of use of ultraviolet protection agents has also been gradually emphasized. In particular, in a season such as the summer season in which sunlight is strong and skin exposure is increased, it is required to thoroughly reapply an ultraviolet protection agent on a wider body part. As ultraviolet protection products, various products to be applied on skin, such as a sun cream, a sun spray, and a sun stick, have been released. Such products are used to protect skin from sunburn, cancer, or photoaging due to leisure activities and sunlight irradiation. The products should be uniformly applied on skin, should be sufficiently stable chemically and physically during a long-term storage, and should not be easily removed by sweat or water after being applied on the skin. In particular, the products should be non-toxic to skin tissues and should not cause a whitening phenomenon as well as a skin irritation and a skin problem. In this case, the superiority of the products may be evaluated according to a degree to which an excellent ultraviolet blocking function is exhibited.

However, in the conventional method of blocking an ultraviolet ray, there is a limitation in mixing an ultraviolet protection material due to a dispersion force, skin problems, and a whitening phenomenon, and thus, an ultraviolet blocking effect is not very good.

Accordingly, there is an urgent need to develop a method of blocking an ultraviolet ray which does not cause a skin irritation and a whitening phenomenon and has an excellent ultraviolet blocking ability.

DISCLOSURE

Technical Problem

The present invention is directed to providing an ultraviolet protection patch, in which an ultraviolet protection material is not in direct contact with skin, thereby not causing skin problems, an irritation phenomenon, and a whitening phenomenon, and a method of applying the same.

The present invention is also directed to providing an ultraviolet protection patch, which is not delaminated due to physical stimulation because of excellent elasticity thereof and has excellent stiffness without inhibiting movement of an adherend, and a method of applying the same.

The present invention is also directed to providing an ultraviolet protection patch, which has excellent transparency and thus does not degrade visibility of an adherend when being attached to skin, and a method of applying the same.

Technical Solution

According to one embodiment of the present invention, an ultraviolet protection patch includes an ultraviolet protection layer including a support component and an ultraviolet protection agent, and a first shape-retaining layer which is a fiber web provided on one surface of the ultraviolet protection layer.

The support component may include a hydrophilic resin, and the ultraviolet protection layer may be a porous substrate formed of a plurality of first nanofibers including the hydrophilic resin and the ultraviolet protection agent.

The ultraviolet protection patch may further include a second shape-retaining layer which is a fiber web provided on the other surface opposite to the one surface of the ultraviolet protection layer.

The hydrophilic resin may include at least one selected from the group consisting of polyvinyl alcohol (PVA), polyvinylpyrrolidone (PVP), polyethylene oxide (PEO), carboxymethyl cellulose (CMC), a polyacrylic acid (PAA), carboxyl methyl cellulose (CMC), starch, and a hyaluronic acid.

The support component may include a hydrophobic resin, and the ultraviolet protection layer may be a non-porous substrate including the hydrophobic resin and the ultraviolet protection agent.

The hydrophobic resin may include at least one selected from the group consisting of thermoplastic polyurethane resin (TPU), polyacrylonitrile, polyethylene, polypropylene, polystyrene, polyvinylidene fluoride, and polymethyl methacrylate.

The ultraviolet protection layer may include the ultraviolet protection agent in a content of 5 to 110 parts by weight with respect to 100 parts by weight of the support component.

The ultraviolet protection agent may include both an organic ultraviolet protection agent and an inorganic ultraviolet protection agent.

The first shape-retaining layer and the second shape-retaining layer may each independently be a fiber web formed of a plurality of second nanofibers.

The first shape-retaining layer and the second shape-retaining layer may each independently have a thickness of 2 μm to 35 μm and a basis weight of 3 g/m² to 30 g/m².

A basis weight of the first shape-retaining layer to the ultraviolet protection layer and a basis weight of the second shape-retaining layer to the ultraviolet protection layer may each independently be in a range of 1:0.3 to 1:2.5.

The first shape-retaining layer and the second shape-retaining layer may each independently be made of a mixture resin which includes an elastic resin including at least one selected from the group consisting of thermoplastic polyurethane resin (TPU), polymethyl methacrylate (PMMA), and polypyrrole (PPy) and a strength reinforcing resin including at least one selected from the group consisting of polyvinylidene fluoride (PVDF), polystyrene (PS), and polyethersulfone (PES).

The mixture resin may include the elastic resin and the strength reinforcing resin in a weight ratio of 1:0.2 to 1:4.

The ultraviolet protection patch may further include a support member provided on one surface of the first shape-retaining layer.

According to another embodiment of the present invention, a method of applying an ultraviolet protection patch includes performing moisture treatment on at least a portion of the ultraviolet protection patch to dissolve the ultraviolet protection layer and fill at least some pores of the first shape-retaining layer and the second shape-retaining layer and includes attaching the ultraviolet protection patch.

The ultraviolet protection patch may further include a second shape-retaining layer which is a fiber web provided on the other surface opposite to the one surface of the ultraviolet protection layer, and in the filling, the ultraviolet protection layer may be dissolved through the moisture treatment to fill the at least some pores of the first shape-retaining layer and the second shape-retaining layer.

Advantageous Effects

According to the present invention, since an ultraviolet protection patch includes an ultraviolet protection layer and a shape-retaining layer having predetermined physical properties, an ultraviolet protection material is not in direct contact with skin, which does not cause skin problems, an irritation phenomenon, and a whitening phenomenon, and due to excellent elasticity, the ultraviolet protection patch is not delaminated due to physical stimulation and has excellent stiffness without inhibiting movement of an adherend. In addition, since the ultraviolet protection layer and the shape-retaining layer have a predetermined basis weight relationship, the ultraviolet protection patch has excellent transparency and thus does not degrade visibility of an adherend when being attached to the skin.

BEST MODES OF THE INVENTION

Hereinafter, embodiments of the present invention will be described in detail with reference to the accompanying drawings so as to be easily practiced by a person of ordinary skill in the art to which the present invention pertains. It should be understood that the present invention may be embodied in various different forms and is not limited to the following embodiments. Parts irrelevant to description are omitted in the drawings in order to clearly describe the present invention, and like reference numerals refer to like elements throughout the specification.

Figure 1:
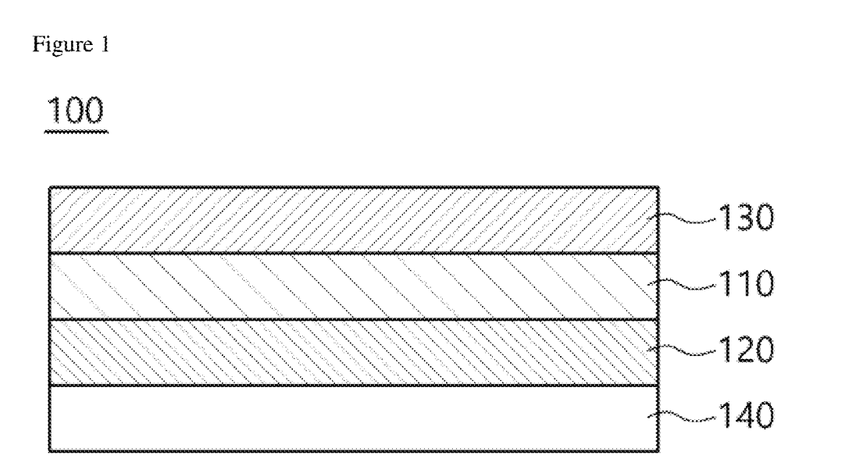
FIG. 1 is a cross-sectional view of an ultraviolet protection patch according to one embodiment of the present invention.
Figure 4:
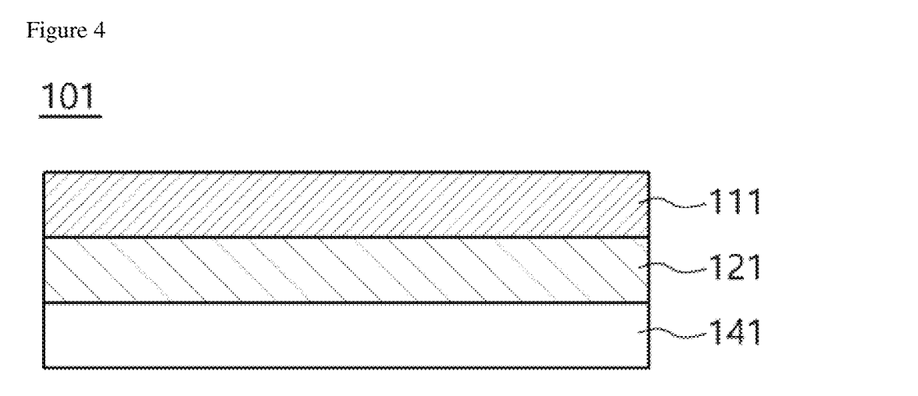
FIG. 4 is a cross-sectional view of an ultraviolet protection patch according to another embodiment of the present invention.

As shown in FIGS. 1 and 4, an ultraviolet protection patch 100 or 101 according to one embodiment of the present invention is implemented to include an ultraviolet protection layer 110 or 111 and a first shape-retaining layer 120 or 121 which is a fiber web provided on one surface of the ultraviolet protection layer.

First, the ultraviolet protection layers 110 and 111 perform a function of exhibiting an ultraviolet blocking ability.

Figure 3:
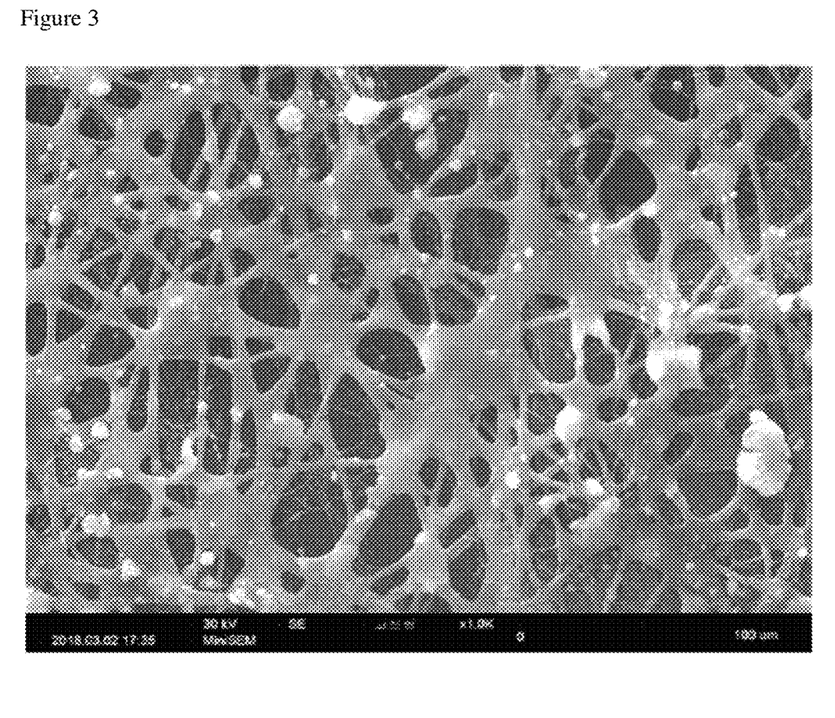
FIG. 3 is a SEM image of an ultraviolet protection layer provided in the ultraviolet protection patch according to one embodiment of the present invention.

As shown in FIG. 3, the ultraviolet protection layer 110 may have a three-dimensional network structure formed by randomly and three-dimensionally stacking one or more strands of first nanofibers.

In addition, according to one embodiment of the present invention, the ultraviolet protection layer 110 may include a support component and an ultraviolet protection agent, and the support component may include a hydrophilic resin.

Since the support component of the ultraviolet protection layer 110 includes the hydrophilic resin, when moisture treatment is performed on the ultraviolet protection patch 100 according to the present invention, the ultraviolet protection layer 110 is dissolved such that the first shape-retaining layer 120 and a second shape-retaining layer 130 to be described below are filled with the ultraviolet protection agent, thereby exhibiting ultraviolet blocking performance.

Meanwhile, the ultraviolet protection layer may be a porous substrate formed of the plurality of first nanofibers formed to include a hydrophilic resin and an ultraviolet protection agent. As described above, when the ultraviolet protection layer is the porous substrate and when moisture treatment is performed on the ultraviolet protection patch 100, moisture can easily permeate into the ultraviolet protection layer, and thus, the ultraviolet protection layer can be more easily dissolved.

The hydrophilic resin may be used without limitation as long as the hydrophilic resin is a hydrophilic resin dissolvable in water and commonly usable in the art. The hydrophilic resin may include at least one selected from the group consisting of polyvinyl alcohol (PVA), polyvinylpyrrolidone (PVP), polyethylene oxide (PEO), carboxymethyl cellulose (CMC), a polyacrylic acid (PAA), carboxyl methyl cellulose (CMC), starch, and a hyaluronic acid. More preferably, PVP may be used.

Figure 5:
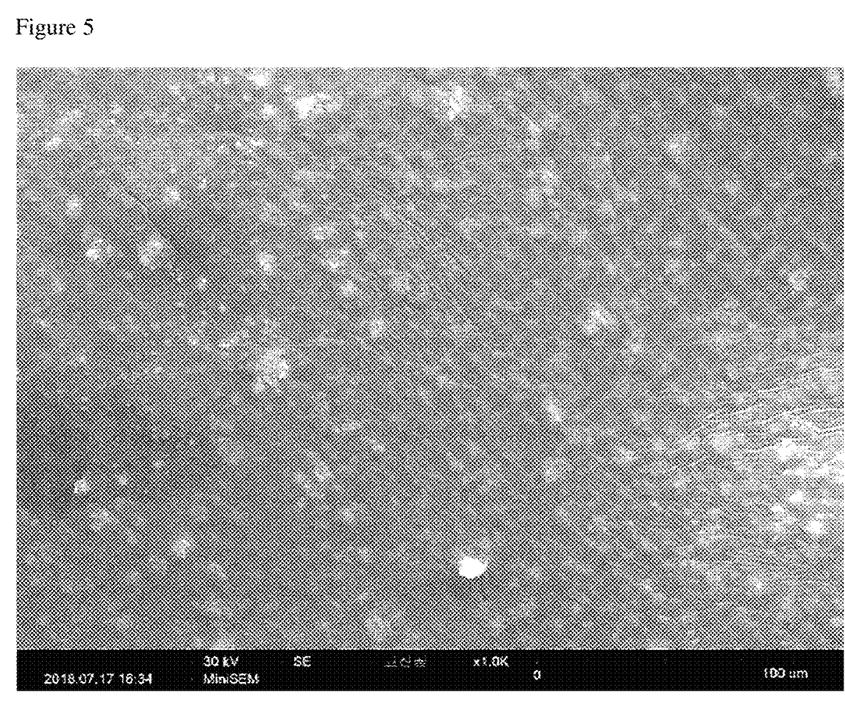
FIG. 5 is an SEM image of an ultraviolet protection layer provided in the ultraviolet protection patch according to another embodiment of the present invention.

Meanwhile, according to another embodiment of the present invention, as shown in FIG. 5, the ultraviolet protection layer 111 according to the present invention may have the shape of a non-porous film not having pores. As an example, the ultraviolet protection layer 111 may have a non-porous film shape formed by randomly stacking one or more strands of nanofibers three-dimensionally to form a three-dimensional network structure and then forming the three-dimensional network structure into a film through a lamination process. Alternatively, the ultraviolet protection layer 111 may have a non-porous film shape formed on the first shape-retaining layer 121 through spray coating.

In addition, since the ultraviolet protection layer 111 includes an ultraviolet protection agent and has a film-shaped structure to have excellent transparency, when the ultraviolet protection patch is attached to skin, visibility of an adherend is not degraded, and an ultraviolet protection material is also not in direct contact with the skin, thereby exhibiting ultraviolet blocking performance without causing skin problems, an irritation phenomenon, and a whitening phenomenon.

In addition, according to one embodiment of the present invention, the ultraviolet protection layer 111 includes a support component and the ultraviolet protection agent, and the support component may include a hydrophobic resin.

The hydrophobic resin may be used without limitation as long as the hydrophobic resin is a hydrophobic resin commonly usable in the art. Preferably, a hydrophobic resin, which is not soluble in water and is soluble in an organic solvent, may be used, more preferably, the hydrophobic resin may include at least one selected from the group consisting of thermoplastic polyurethane resin (TPU), polyacrylonitrile, polyethylene, polypropylene, polystyrene, polyvinylidene fluoride, and polymethyl methacrylate, and still more preferably, TPU may be used.

Meanwhile, the ultraviolet protection agent may be used without limitation as long as the ultraviolet protection agent is an ultraviolet protection agent commonly usable in the art. The ultraviolet protection agent may preferably include at least one selected from the group consisting of an organic ultraviolet protection agent and an inorganic ultraviolet protection agent and may more preferably include both of the organic ultraviolet protection agent and the inorganic ultraviolet protection agent. Accordingly, a sun protection factor may be more excellent.

The organic ultraviolet protection agent may be used without limitation as long as the organic ultraviolet protection agent is an organic ultraviolet protection agent commonly usable in the art. Preferably, the organic ultraviolet protection agent may include at least one selected from the group consisting of methylene bis-benzotriazolyl tetramethylbutylphenol (MBBT), bis-ethylhexyloxyphenol methoxyphenyl triazine (BEMT), polysilicon-15, butyl methoxydibenzoylmethane, octocrylene, a phenylbenzimidazolesulfonic acid, and ethylhexylmethoxycinnamate. In addition, the inorganic ultraviolet protection agent may be used without limitation as long as the inorganic ultraviolet protection agent is an inorganic ultraviolet protection agent commonly usable in the art. The inorganic ultraviolet protection agent may include at least one selected from the group consisting of titanium dioxide ($TiO_2$), zinc oxide (ZnO), iron oxide ($Fe_2O_3$), zirconium oxide ($ZrO_2$), silicon dioxide ($SiO_2$), manganese oxide (MnO), aluminum oxide ($Al_2O_3$), cerium oxide ($CeO_3$), and mica.

The ultraviolet protection agent may be included in a content of 5 to 110 parts by weight and preferably 10 to 100 parts by weight with respect to 100 parts by weight of the hydrophilic resin. When the content of the ultraviolet protection agent is less than 5 parts by weight with respect to 100 parts by weight of the hydrophilic resin, ultraviolet blocking performance may be degraded. When the content of the ultraviolet protection agent exceeds 110 parts by weight, the ultraviolet protection material may be in contact with skin, which may cause skin problems, an irritation phenomenon, and a whitening phenomenon, and the opacity of the ultraviolet protection patch may be increased.

Meanwhile, when the ultraviolet protection layer 110 is a porous substrate, the first nanofibers may have a predetermined fiber average diameter such that a bonding force with the first shape-retaining layer 120 and the second shape-retaining layer 130 is not lowered, and the present invention is not necessarily limited thereto.

In addition, the ultraviolet protection layers 110 and 111 may have a thickness of 1 µm to 35 µm and preferably a thickness of 2 µm to 30 µm. When the thickness of the ultraviolet protection layer is less than 1 µm, ultraviolet blocking performance may be degraded. When the thickness of the ultraviolet protection layer exceeds 35 µm and the ultraviolet protection layer is a porous substrate, the ultraviolet protection material may be in contact with skin during moisture treatment, which may cause skin problems, an irritation phenomenon, and a whitening phenomenon, and due to physical stimulation, delamination may be caused or movement of an adherend may be inhibited.

The ultraviolet protection layers 110 and 111 may have a basis weight of 1 $g/m^2$ to 25 $g/m^2$ and preferably a basis weight of 4 $g/m^2$ to 20 $g/m^2$. When the content range of the ultraviolet protection agent and the thickness range of the ultraviolet protection layer are satisfied, but when the basis weight of the ultraviolet protection layer 110 is less than 1 $g/m^2$, ultraviolet blocking performance may be degraded, and the ultraviolet protection patches 100 and 101 may be delaminated due to physical stimulation caused by movement or the like. When the basis weight exceeds 30 $g/m^2$, the ultraviolet protection material may be in contact with skin, which may cause skin problems and skin irritation, the opacity of the ultraviolet protection patch may be increased, and movement of an adherend may be inhibited.

Meanwhile, the ultraviolet protection patch according to one embodiment of the present invention may further include the second shape-retaining layer 130 which is a fiber web provided on the other surface opposite to one surface of the ultraviolet protection layer 110.

The first shape-retaining layers 120 and 121 and the second shape-retaining layer 130 function to improve the elasticity, adhesion, and strength of the ultraviolet protection patches.

Figure 2:
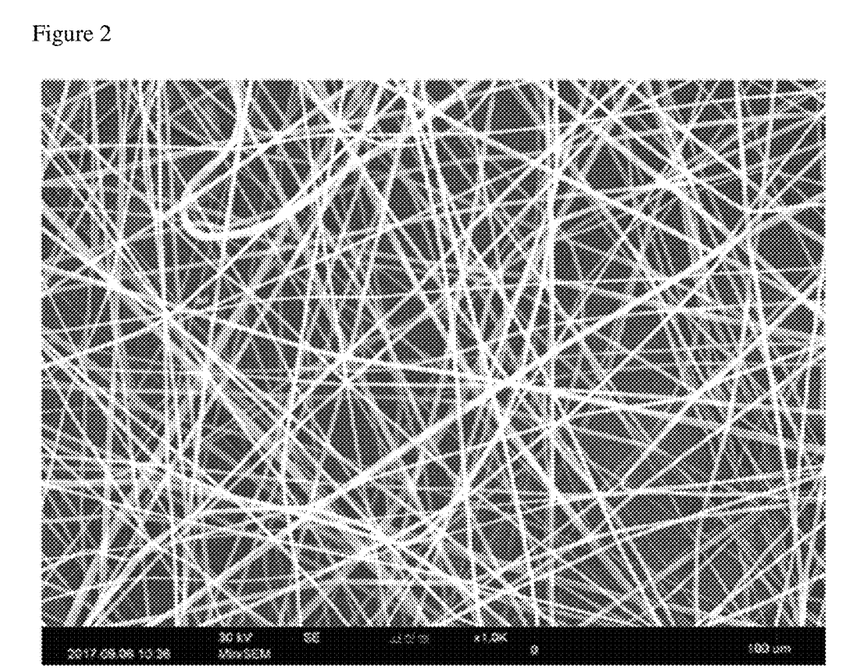
FIG. 2 is a scanning electron microscope (SEM) image of a shape-retaining layer provided in the ultraviolet protection patch according to one embodiment of the present invention.

The first shape-retaining layers 120 and 121 and the second shape-retaining layer 130 may each independently be a fiber web having a three-dimensional network structure formed by randomly stacking one or more strands of second nanofibers three-dimensionally as shown in FIG. 2.

In addition, the first shape-retaining layer 120 and the second shape-retaining layer 130 may be porous substrates such that the first shape-retaining layer 120 and the second shape-retaining layer 130 are filled with the ultraviolet protection agent provided in the ultraviolet protection layer when moisture treatment is performed on the ultraviolet protection patch 100 to dissolve the ultraviolet protection layer 110. Since the first shape-retaining layer 120 and the second shape-retaining layer 130 are filled with the ultraviolet protection agent, a protection material may not be in direct contact with skin, thereby exhibiting an effect of preventing skin problems, an irritation phenomenon, and a whitening phenomenon.

Each of the first shape-retaining layers 120 and 121 and the second shape-retaining layer 130 may be made of a mixture resin including an elastic resin and a strength reinforcing resin.

The elastic resin may be used without limitation as long as the elastic resin is an elastic resin commonly usable in the art. Preferably, the elastic resin may include at least one selected from the group consisting of TPU, polymethyl methacrylate (PMMA), and polypyrrole (PPy). More preferably, the elastic resin may include TPU. In addition, the strength reinforcing resin may be used without limitation as long as the strength reinforcing resin is a strength reinforcing resin commonly useable in the art. Preferably, the strength reinforcing resin may include at least one selected from the group consisting of polyvinylidene fluoride (PVDF), polystyrene (PS), and polyethersulfone (PES). Since the above-described resins are used as the elastic resin and the strength reinforcing resin, the ultraviolet protection patch may have excellent transparency and thus may exhibit an effect of not reducing the visibility of an adherend when being attached to skin.

In addition, the mixture resin may include the elastic resin and the strength reinforcing resin in a weight ratio of 1:0.2 to 1:4 and preferably in a weight ratio of 1:0.5 to 1:3. When the weight ratio of the elastic resin to the strength reinforcing resin is less than 1:0.2, the strength of the ultraviolet protection patch may be decreased, and when the weight ratio exceeds 1:4, the elasticity and adhesion of the ultraviolet protection patch may be decreased.

In addition, the first shape-retaining layers 120 and 121 and the second shape-retaining layer 130 may each independently have a thickness of 2 μm to 35 μm and preferably a thickness of 3 μm to 30 μm. When the first shape-retaining layers 120 and 121 and the second shape-retaining layer 130 satisfy a basis weight range to be described below but each have a thickness that is less than 2 μm, adhesion and/or elasticity may be decreased. When the thickness of each of the first shape-retaining layers 120 and 121 and the second shape-retaining layer 130 exceeds 35 μm, the ultraviolet protection material may be in contact with skin, which may cause skin problems, an irritation phenomenon, and a whitening phenomenon, and the stiffness of the ultraviolet protection patch may be decreased.

In addition, when the ultraviolet protection layer 110 is a porous substrate, the first shape-retaining layer 120 and the second shape-retaining layer 130 may each independently have a predetermined pore diameter that is smaller than an average particle diameter of the inorganic ultraviolet protection agent that may be provided in the above-described ultraviolet protection agent. As a result, the ultraviolet protection material may not be in direct contact with skin, which may not cause skin problems, an irritation phenomenon, and a whitening phenomenon, and due to excellent elasticity, it is possible to exhibit an effect in which delamination is not caused due to physical stimulation or movement of an adherend is not inhibited.

In addition, when the ultraviolet protection layer 111 is a non-porous substrate, since the ultraviolet protection layer 111 has a solidified film shape, the inorganic ultraviolet protection agent may not pass through the first shape-retaining layer 121 to not be in contact with skin, and thus, the ultraviolet protection layer 111 may have a predetermined pore diameter irrespective of a particle diameter of the inorganic ultraviolet protection agent. Accordingly, the present invention is not particularly limited thereto.

In addition, the first shape-retaining layers 120 and 121 and the second shape-retaining layer 130 may each independently have a basis weight of 3 g/m² to 30 g/m² and preferably a basis weight of 4 g/m² to 20 g/m². When the first shape-retaining layers 120 and 121 and the second shape-retaining layer 130 each satisfy the thickness but each have a basis weight that is less than 3 g/m², the ultraviolet protection material may be in contact with skin, which may cause skin problems, an irritation phenomenon, and a whitening phenomenon, and the elasticity, adhesion, and/or strength of the ultraviolet protection patches 100 and 101 may be decreased. When the basis weight exceeds 30 g/m², the ultraviolet protection patches 100 and 101 may be delaminated due to physical stimulation caused by movement or the like, and movement of an adherend may be inhibited.

Meanwhile, a basis weight ratio of the first shape-retaining layer 120 to the ultraviolet protection layer 110 and a basis weight ratio of the second shape-retaining layer 130 to the ultraviolet protection layer 110 may each independently be in a range of 1:0.3 to 1:2.5 and preferably in a range of 1:0.5 to 1:2. When the basis weight ratio is less than 1:0.3, ultraviolet blocking performance may be degraded, the ultraviolet protection patch may be delaminated due to physical stimulation caused by movement or the like, and movement of an adherend may be inhibited. In addition, when the basis weight ratio exceeds 1:2.5, skin problems and an irritation phenomenon may be caused, the opacity of the ultraviolet protection patch may be increased, the elasticity, adhesion, and strength of the ultraviolet protection patch may be decreased, and due to physical stimulation, the ultraviolet protection patch may be delaminated or movement of an adherend may be inhibited.

Meanwhile, the ultraviolet protection patch 100 or 101 according to the present invention may further include a support member 140 or 141 provided on one surface of the first shape-retaining layer 120 or 121.

The support members 140 and 141 may function to support the ultraviolet protection patches 100 and 101 and may include any material without limitation as long as the material may be commonly used for a support member in the art. Preferably, the support members 140 and 141 may include at least one selected from the group consisting of silicon, polyethylene terephthalate (PET), polypropylene (PP), and polyurethane (PU).

In addition, the support members 140 and 141 may be porous members, and as an example, the support member 140 may be a nonwoven fabric, a fabric, or a textile.

The fabric means that a fiber included in the fabric has longitudinal and transverse directionalities. A specific structure of the fabric may be a plain weave, a twilled weave, or the like, and a density of warp yarn and weft yarn is not particularly limited. In addition, a knitted fabric may have a known knit structure and may be a weft knitted fabric, a warp knitted fabric, or the like. As an example, a raw fabric may be a tricot in which yarn is warp knitted. In addition, the support member 140 may be a nonwoven fabric in which a fiber has no longitudinal or transverse directionality. The support member 140 may include a known nonwoven fabric manufactured through various methods, such as a dry nonwoven fabric such as a chemical bonding nonwoven fabric, a thermal bonding nonwoven fabric, or an airlaid nonwoven fabric, a wet nonwoven fabric, a spunlace nonwoven fabric, a needle punching nonwoven fabric, or a meltblown nonwoven fabric.

Meanwhile, according to another embodiment of the present invention, the ultraviolet protection patch according to the present invention may further include an adhesion reinforcing layer (not shown) for reinforcing adhesion between the first shape-retaining layer 120 or 121 and the support member 140 or 141.

In this case, the adhesion reinforcing layer may be formed through third nanofibers including the above-describe hydrophilic resin.

Meanwhile, the present invention provides a method of applying an ultraviolet protection patch including performing moisture treatment on at least a portion of the above-described ultraviolet protection patch to dissolve the ultraviolet protection layer 110 and fill at least some pores of the first shape-retaining layer 120 and attaching the ultraviolet protection patch.

Meanwhile, the ultraviolet protection layer 110 may further include the second shape-retaining layer which is a fiber web provided on the other surface opposite to the one surface as described above, and in the filling, the ultraviolet protection layer may be dissolved through the moisture treatment to fill at least some pores of the first shape-retaining layer and the second shape-retaining layer.

The moisture treatment may be performed using a known aqueous solution or aqueous dispersion including moisture, such as a known essence and moisturizer. A hydrophilic polymer provided in the ultraviolet protection layer 110 may be dissolved through the moisture treatment to fill at least some pores of each of the first shape-retaining layer 120 and the second shape-retaining layer 130, thereby exhibiting ultraviolet blocking performance.

In this case, a sequence between an operation of filling the pores and an operation of attaching the ultraviolet protection patch may be changed according to a user's convenience, and the present invention is not limited thereto.

The ultraviolet protection patches 100 and 101 according to the present invention may be manufactured through a manufacturing method to be described below, but the present invention is not limited thereto.

First, operations of manufacturing the ultraviolet protection patch 100 including the ultraviolet protection layer 110, which is a porous substrate, will be described.

The ultraviolet protection patch 100 including the ultraviolet protection layer 110, which is the porous substrate, may be manufactured by forming the first shape-retaining layer 120 on one surface of the support member 140, forming the second shape-retaining layer 130, forming the ultraviolet protection layer 110, and sequentially stacking and laminating the support member 140, the first shape-retaining layer 120, the ultraviolet protection layer 110, and the second shape-retaining layer 130.

First, an operation of forming the first shape-retaining layer 120 on one surface of the support member 140 and an operation of forming the second shape-retaining layer 130 will be described.

As described above, the first shape-retaining layer 120 and the second shape-retaining layer 130 may be made of a mixture resin including an elastic resin and a strength reinforcing resin. Specifically, the first shape-retaining layer 120 and the second shape-retaining layer 130 may be formed by preparing a spinning solution including a solvent and the mixture resin at a temperature of 60° C. to 100° C. and preferably at a temperature of 65° C. to 95° C. and then electrospinning the spinning solution.

In this case, the solvent may be used without limitation as long as the solvent is a solvent commonly usable in the art. The solvent may preferably include at least one selected from the group consisting of dimethylacetamide and acetone, may more preferably include both dimethylacetamide and acetone, may still more preferably dimethylacetamide and acetone in a weight ratio of 9.5:0.5 to 5:5, and may most preferably include dimethylacetamide and acetone in a weight ratio of 9:1 to 7:3. In addition, the spinning solution may include the solvent in a content of 300 to 800 parts by weight and preferably 350 to 750 parts by weight with respect to 100 parts by weight of the mixture resin.

In addition, the electrospinning may be performed using any electrospinning method without limitation as long as the electrospinning method is commonly usable in the art. As an example, as an electrospinning device, an electrospinning device including a single spin pack with one spin nozzle may be used, or an electrospinning device including a plurality of single spin packs or including a spin pack with a plurality of nozzles may be used for mass production. In addition, in an electrospinning method, dry spinning or wet spinning with an external coagulation bath may be used, and a method is not limited.

The electrospinning may be used without limitation as long as the electrospinning is performed under electrospinning conditions commonly usable in the art. As an example, the electrospinning may be performed under conditions of an applied voltage of 10 kV to 40 kV, a distance of 10 cm to 30 cm between a spin nozzle and a current collector, a discharge rate per minute of 0.3 to 0.7 cc/g/hole, a temperature of 15° C. to 45° C., and a relative humidity of 35% to 65% and preferably under conditions of an applied voltage of 15 kV to 35 kV, a distance of 15 cm to 25 cm between a spin nozzle and a current collector, a discharge rate per minute of 0.3 to 0.65 cc/g/hole, a temperature of 20° C. to 40° C., and a relative humidity of 40% to 60%.

Next, an operation of forming the ultraviolet protection layer 110 will be described.

As described above, the ultraviolet protection layer 110 may be formed to include a hydrophilic resin and an ultraviolet protection agent. Specifically, the ultraviolet protection layer 110 may be formed by preparing a spinning solution including a hydrophilic resin, an ultraviolet protection agent, and a solvent at a temperature of 60° C. to 100° C. and preferably at a temperature of 65° C. to 95° C. and then electrospinning the spinning solution.

In this case, the solvent may be used without limitation as long as the solvent is a solvent commonly usable in the art. The solvent may preferably include at least one selected from the group consisting of dimethylacetamide and acetone and may more preferably include dimethylacetamide. In addition, the spinning solution may include the solvent in a content of 550 to 1,050 parts by weight and preferably 600 to 1,000 parts by weight with respect to 100 parts by weight of the hydrophilic resin.

In addition, the electrospinning may be performed using any electrospinning method without limitation as long as the electrospinning method is commonly usable in the art. As an example, as an electrospinning device, an electrospinning device including a single spin pack with one spin nozzle may be used, or an electrospinning device including a plurality of single spin packs or including a spin pack with a plurality of nozzles may be used for mass production. In addition, in an electrospinning process, dry spinning or wet spinning with an external coagulation bath may be used, and a method is not limited.

The electrospinning may be used without limitation as long as the electrospinning is performed under electrospinning conditions commonly usable in the art. As an example, the electrospinning may be performed under conditions such of an applied voltage of 10 kV to 40 kV, a distance of 10 cm to 30 cm between a spin nozzle and a current collector, a discharge rate per minute of 0.35 to 0.75 cc/g/hole, a temperature of 15° C. to 45° C., and a relative humidity of 25% to 55% and preferably under conditions of an applied voltage of 15 kV to 35 kV, a distance of 15 cm to 25 cm between a spin nozzle and a current collector, a discharge rate per minute of 0.40 to 0.70 cc/g/hole, a temperature of 20° C. to 40° C., and a relative humidity of 30% to 50%.

Next, an operation of sequentially stacking and laminating the support member 140, the first shape-retaining layer 120, the ultraviolet protection layer 110, and the second shape-retaining layer 130 will be described.

The laminating may be performed using any laminating method without limitation as long as the laminating method is a laminating method commonly usable in the art, and as a non-limiting example thereof, the laminating may be performed through a typical lamination process. In this case, a temperature condition may be in a range of 60° C. to 100° C. and preferably in a range of 70° C. to 90° C.

Next, operations of manufacturing the ultraviolet protection patch 101 including the ultraviolet protection layer 111, which is a non-porous substrate, will be described.

In order to manufacture the ultraviolet protection patch 101 including the ultraviolet protection layer 111 which is the non-porous substrate, the ultraviolet protection patch 101 including the ultraviolet protection layer 111 may be manufactured by forming the first shape-retaining layer 121 on one surface of the support member 141, forming an ultraviolet protection layer-forming member, sequentially stacking and laminating the support member 141, the first shape-retaining layer 121, and the ultraviolet locking layer-forming member, and forming the ultraviolet locking layer-forming member into a film to form the ultraviolet protection layer 111.

The same contents as those described in the method of manufacturing the ultraviolet protection patch 100 including the ultraviolet protection layer 110, which is the porous substrate described above, will be omitted, and a method of manufacturing the ultraviolet protection patch 101 including the ultraviolet protection layer 111, which is the non-porous substrate, will be described below.

The ultraviolet protection layer-forming member may be formed to include a hydrophobic resin and an ultraviolet protection material. Specifically, the ultraviolet protection layer-forming member may be formed by preparing a spinning solution including a hydrophobic resin, an ultraviolet protection agent, and a solvent at a temperature of 105° C. to 155° C. and preferably at a temperature of 110° C. to 150° C. and then electrospinning the spinning solution.

The solvent may be used without limitation as long as the solvent is a solvent commonly usable in the art. The solvent may preferably include at least one selected from the group consisting of dimethylacetamide and acetone and may more preferably include dimethylacetamide. In addition, the spinning solution may include the solvent in a content of 550 to 1,050 parts by weight and preferably 600 to 1,000 parts by weight with respect to 100 parts by weight of the hydrophobic resin.

In this case, a concentration of the spinning solution may be relatively lower than that of the spinning solution for forming the first shape-retaining layer, and thus, only the ultraviolet protection layer may be selectively formed into a film when a lamination process is performed.

Next, an operation of manufacturing the ultraviolet protection patch 101 including the ultraviolet protection layer 111 formed by sequentially stacking and laminating the support member 141, the first shape-retaining layer 121, and the ultraviolet protection layer-forming member and forming the ultraviolet protection layer-forming member into the film will be described.

By performing the laminating, the hydrophobic resin of the ultraviolet protection layer-forming member may be plasticized to form the ultraviolet protection layer-forming member into the film, thereby forming the non-porous ultraviolet protection layer 111.

Modes of the Invention

The present invention will be described in more detail through the following examples, but the following examples do not limit the scope of the present invention, and it should be understood that the following examples are intended to assist the understanding of the present invention.

Example 1: Ultraviolet Protection Patch Using Hydrophilic Polymer (1) Formation of Ultraviolet Protection Layer First, in order to form an ultraviolet protection layer, a solution including dimethylacetamide as a solution in a content of 800 parts by weight with respect to 100 parts by weight of PVP with a weight average molecular weight of 500,000 as a hydrophilic resin was prepared under a temperature condition of 80° C., and then, an ultraviolet protection agent, which includes an organic ultraviolet protection agent and an inorganic ultraviolet protection agent in a weight ratio of 1:0.5 wherein the organic ultraviolet protection agent includes a first organic ultraviolet agent (PARSOL 1789) and a second organic ultraviolet protection agent (PARSOL 340) in a weight ratio of 1:1 and the inorganic ultraviolet protection agent includes particles of titanium dioxide ($TiO_2$), was mixed into the solution in a content of 55 parts by weight with respect to 100 parts by weight of the hydrophilic resin, thereby preparing a spinning solution. The prepared spinning solution was transferred to a spin pack, electrospinning was performed thereon under conditions of an applied voltage of 25 kV, a distance of 20 cm between a spin nozzle and a current collector, a discharge rate per minute of 0.55 cc/g/hole, a temperature of 30° C., and a relative humidity of 40% to form a substrate having a web shape formed of first nanofibers with an fiber average diameter of 250 nm, and then, heat treatment was performed in a hot blast furnace at a temperature of 60° C. for 30 minutes to remove residual solvents, thereby forming the ultraviolet protection layer. The prepared ultraviolet protection layer had a thickness of 6 μm and a basis weight of 10 g/m$^2$.

2) Formation of First Shape-Retaining Layer and Second Shape-Retaining Layer

Next, in order to form a first shape-retaining layer and a second shape-retaining layer, after a spinning solution, which includes a solution in a content of 566 parts by weight with respect to 100 parts by weight of a mixture resin including TPU with a weight average molecular weight of 150,000 as an elastic resin and PVDF with a weight average molecular weight of 250,000 as a strength reinforcing resin in a weight ratio of 1:1 wherein the solution includes dimethylacetamide and acetone in a weight ratio of 7:3, was prepared under a temperature condition of 80° C., the prepared spinning solution was transferred to a spin pack, electrospinning was performed thereon under conditions of an applied voltage of 25 kV, a distance of 20 cm between a spin nozzle and a current collector, a discharge rate per minute of 0.5 cc/g/hole, a temperature of 30° C., and a relative humidity of 50%, thereby forming the first shape-retaining layer and the second shape-retaining layer which are formed of second nanofibers with an fiber average diameter of 350 nm. The formed first and second shape-retaining layers each had a thickness of 15 μm and a basis weight of 15 g/m².

In this case, the first shape-retaining layer was formed by being spun directly on a nonwoven fabric having a basis weight of 30 g/m² as a support member with a current collector, and the second shape-retaining layer was formed by being spun directly on a release paper with a current collector.

(3) Manufacture of Ultraviolet Protection Patch

The support member, the first shape-retaining layer, the ultraviolet protection layer, and the second shape-retaining layer were disposed to be sequentially stacked, and then, an ultraviolet protection patch was manufactured at a temperature of 80° C. through simplified lamination.

Examples 2 to 17

Ultraviolet protection patches as shown in Tables 1 to 3 below were manufactured in the same manner as in Example 1 except that a content of an ultraviolet protection agent, a thickness and a basis weight of a first shape-retaining layer and a second shape-retaining layer, a basis weight of an ultraviolet protection layer, and the like were changed.

Experimental Example 1

The ultraviolet protection patches prepared according to Examples 1 to 17 were treated with moisturizers (Liponic EG-1, Lubraj el DV-Free, and deionized (DI) water) to dissolve the ultraviolet protection layer and fill pores with moisture and the ultraviolet protection agent, and then, the following items were measured, and the measured results are shown in Tables 1 to 3 below.

1. Measurement of Sun Protection Factor (SPF)

The ultraviolet protection patches according to Examples 1 to 17, in which the pores of the first shape-retaining layer and the second shape-retaining layer were filled with moisture and the ultraviolet protection agent, were cut to a size of 5 cm×5 cm and attached onto a PMMA plate. Then, SPF values were measured with respect to a monochromatic protection factor graph at a wavelength of 290 nm to 400 nm using an SPF measuring device (SPF-290AS manufactured by Solar Light Company). In this case, five points were measured to show an average value.

2. Evaluation of Exposure of Ultraviolet Protection Agent

In the ultraviolet protection patches according to Examples 1 to 17 in which the pores of the first shape-retaining layer and the second shape-retaining layer were filled with moisture and the ultraviolet protection agent, whether the ultraviolet protection agent was exposed to the outside was evaluated in such a manner that the mark "○" is indicated that the ultraviolet protection agent was not exposed to the outside from the first shape-retaining layer and/or the second shape-retaining layer of the ultraviolet protection patch and the mark "x" is indicated that the ultraviolet protection agent was not exposed to the outside.

3. Evaluation of Visibility of Adherend

The ultraviolet protection patches according to Examples 1 to 17, in which the pores of the first shape-retaining layer and the second shape-retaining layer were filled with moisture and the ultraviolet protection agent, were attached to skin, and visibility of an adhered was evaluated on 30 workers with over ten years' experience in the related industry (1—very bad, 2—bad, 3—slightly bad, 4—medium, 5—slightly good, 6—good, and 7—very good).

4. Evaluation of Adhesion and Elasticity

The ultraviolet protection patches according to Examples 1 to 17, in which the pores of the first shape-retaining layer and the second shape-retaining layer were filled with moisture and the ultraviolet protection agent, were attached to skin, and adhesion (delamination due to physical stimulation) and elasticity (inhibition of movement of an adherend) were comprehensively evaluated on 30 workers with over ten years' experience in the related industry (1—very bad, 2—bad, 3—slightly bad, 4—medium, 5—slightly good, 6—good, and 7—very good).

TABLE 1

| Classification | | Example 1 | Example 2 | Example 3 | Example 4 | Example 5 | Example 6 |
|---|---|---|---|---|---|---|---|
| First shape-retaining layer | Thickness (μm) | 15 | 1 | 3 | 30 | 40 | 15 |
| | Basis weight (g/m²) | 15 | 15 | 15 | 15 | 15 | 1 |
| Second shape-retaining layer | Thickness (μm) | 15 | 1 | 3 | 30 | 40 | 15 |
| | Basis weight (g/m²) | 15 | 15 | 15 | 15 | 15 | 1 |
| Ultraviolet protection layer | Content of ultraviolet protection agent (parts by weight) | 55 | 55 | 55 | 55 | 55 | 55 |
| | Type of ultraviolet protection agent | Organic and inorganic mixture | Organic and inorganic mixture | Organic and inorganic mixture | Organic and inorganic mixture | Organic and inorganic mixture | Organic and inorganic mixture |
| | Basis weight (g/m²) | 10 | 10 | 10 | 10 | 10 | 10 |
| Basis weight ratio of first shape-retaining layer to ultraviolet protection layer | | 1:0.67 | 1:0.67 | 1:0.67 | 1:0.67 | 1:0.67 | 1:10 |
| Basis weight ratio of second shape-retaining layer to ultraviolet protection layer | | 1:0.67 | 1:0.67 | 1:0.67 | 1:0.67 | 1:0.67 | 1:10 |
| SPF | | 50 or more | 50 or more | 50 or more | 50 or more | 50 or more | 50 or more |
| Exposure prevention of ultraviolet protection agent | | 6.8 | 5.9 | 6.8 | 6.8 | 3.8 | 2.2 |

TABLE 1-continued

| Classification | Example 1 | Example 2 | Example 3 | Example 4 | Example 5 | Example 6 |
|---|---|---|---|---|---|---|
| Visibility of adherend | 6.7 | 6.6 | 6.8 | 6.7 | 6.5 | 6.4 |
| Adhesion and elasticity | 6.8 | 3.3 | 6.6 | 6.7 | 6.2 | 6.3 |

TABLE 2

| Classification | | Example 7 | Example 8 | Example 9 | Example 10 | Example 11 | Example 12 |
|---|---|---|---|---|---|---|---|
| First shape-retaining layer | Thickness (μm) | 15 | 15 | 15 | 15 | 15 | 15 |
| | Basis weight (g/m$^2$) | 4 | 20 | 35 | 15 | 15 | 15 |
| Second shape-retaining layer | Thickness (μm) | 15 | 15 | 15 | 15 | 15 | 15 |
| | Basis weight (g/m$^2$) | 4 | 20 | 35 | 15 | 15 | 15 |
| Ultraviolet protection layer | Content of ultraviolet protection agent (parts by weight) | 55 | 55 | 55 | 3 | 10 | 100 |
| | Type of ultraviolet protection agent | Organic and inorganic mixture | Organic and inorganic mixture | Organic and inorganic mixture | Organic and inorganic mixture | Organic and inorganic mixture | Organic and inorganic mixture |
| | Basis weight (g/m$^2$) | 8 | 10 | 9 | 10 | 10 | 10 |
| Basis weight ratio of first shape-retaining layer to ultraviolet protection layer | | 1:2 | 1:0.5 | 1:0.26 | 1:0.67 | 1:0.67 | 1:0.67 |
| Basis weight ratio of second shape-retaining layer to ultraviolet protection layer | | 1:2 | 1:0.5 | 1:0.26 | 1:0.67 | 1:0.67 | 1:0.67 |
| SPF | | 50 or more | 50 or more | 50 or more | less than 50 | 50 or more | 50 or more |
| Exposure prevention of ultraviolet protection agent | | 6.7 | 6.7 | 6.6 | 6.6 | 6.7 | 6.4 |
| Visibility of adherend | | 6.7 | 6.6 | 6.3 | 6.5 | 6.6 | 6.5 |
| Adhesion and elasticity | | 6.6 | 6.5 | 2.1 | 6.8 | 6.8 | 6.6 |

TABLE 3

| Classification | | Example 13 | Example 14 | Example 15 | Example 16 | Example 17 |
|---|---|---|---|---|---|---|
| First shape-retaining layer | Thickness (μm) | 15 | 15 | 15 | 15 | 10 |
| | Basis weight (g/m$^2$) | 15 | 150 | 5 | 15 | 10 |
| Second shape-retaining layer | Thickness (μm) | 15 | 15 | 15 | 15 | 10 |
| | Basis weight (g/m$^2$) | 15 | 15 | 5 | 15 | 10 |
| Ultraviolet protection layer | Content of ultraviolet protection agent (parts by weight) | 130 | 20 | 55 | 55 | 55 |
| | Type of ultraviolet protection agent | Organic and inorganic mixture | Organic and inorganic mixture | Organic and inorganic mixture | Organic and inorganic mixture | Organic and inorganic mixture |
| | Basis weight (g/m$^2$) | 10 | 0.5 | 4 | 20 | 30 |
| Basis weight ratio of first shape-retaining layer to ultraviolet protection layer | | 1:0.67 | 1:0.03 | 1:0.8 | 1:1.33 | 1:3 |
| Basis weight ratio of second shape-retaining layer to ultraviolet protection layer | | 1:0.67 | 1:0.03 | 1:0.8 | 1:1.33 | 1:3 |

TABLE 3-continued

| Classification | Example 13 | Example 14 | Example 15 | Example 16 | Example 17 |
|---|---|---|---|---|---|
| SPF | 50 or more | less than 50 | 50 or more | 50 or more | 50 or more |
| Exposure prevention of ultraviolet protection agent | 3.8 | 6.7 | 6.6 | 6.7 | 2.8 |
| Visibility of adherend | 3.0 | 6.8 | 6.8 | 6.7 | 2.6 |
| Adhesion and elasticity | 6.7 | 3.8 | 6.8 | 6.6 | 5.9 |

As can be seen from Tables 1 to 3, in Examples 1, 3, 4, 7, 8, 11, 12, 15, and 16, which satisfy all of a content of the ultraviolet protection agent, a thickness and basis weight of the first shape-retaining layer and the second shape-retaining layer, and a basis weight of the ultraviolet protection layer according to the present invention, it can be confirmed through an effect of the excellent visibility of the adherend and an effect of the excellent adhesion and elasticity that effects, in which movement of the adherend is not inhibited even on an uneven surface of the adherend, the SPF is high, and the ultraviolet protection agent is not exposed to the outside, are all exhibited at the same time as compared with Examples 2, 5, 6, 9, 10, 13, 14, and 17 which do not satisfy any one among these.

Example 18: Ultraviolet Protection Patch Using Hydrophobic Polymer (1) Formation of Ultraviolet Protection Layer-Forming Member First, in order to form an ultraviolet protection layer-forming member, a solution, which includes a solvent in a content of a total of 900 parts by weight with respect to 100 parts by weight of TPU with a weight average molecular weight of 250,000 as a hydrophobic resin wherein the solvent includes dimethylacetamide and acetone in a weight ratio of 8:2, was prepared under a temperature condition of 130° C., and then, an ultraviolet protection agent, which includes an organic ultraviolet protection agent and an inorganic ultraviolet protection agent in a weight ratio of 1:0.5 wherein the organic ultraviolet protection agent includes a first organic ultraviolet agent (PARSOL 1789) and a second organic ultraviolet protection agent (PARSOL 340) in a weight ratio of 1:1 and the inorganic ultraviolet protection agent includes particles of titanium dioxide ($TiO_2$), was mixed into the solution in a content of 55 parts by weight with respect to 100 parts by weight of the hydrophobic resin, thereby preparing a spinning solution.

The prepared spinning solution was transferred to a spin pack, and electrospinning was performed thereon under conditions of an applied voltage of 25 kV, a distance of 20 cm between a spin nozzle and a current collector, a discharge rate per minute of 0.55 cc/g/hole, a temperature of 30° C., and a relative humidity of 40%, thereby forming the ultraviolet protection layer-forming member formed of nanofibers with an average fiber diameter of 250 nm.

(2) Formation of First Shape-Retaining Layer

Next, in order to form a first shape-retaining layer, after a spinning solution, which includes a solution in a content of a total of 566 parts by weight with respect to 100 parts by weight of a mixture resin including TPU with a weight average molecular weight of 150,000 as an elastic resin and PVDF with a weight average molecular weight of 250,000 as a strength reinforcing resin in a weight ratio of 1:1 wherein the solution includes dimethylacetamide and acetone in a weight ratio of 7:3, was prepared under a temperature condition of 80° C., the prepared spinning solution was transferred to a spin pack, and electrospinning was performed thereon under conditions of an applied voltage of 25 kV, a distance of 20 cm between a spin nozzle and a current collector, a discharge rate per minute of 0.5 cc/g/hole, a temperature of 30° C., and a relative humidity of 50%, thereby forming the first shape-retaining layer formed of nanofibers with an fiber average diameter of 350 nm. The prepared first shape-retaining layer had a thickness of 15 μm, a basis weight of 15 g/m2, and an air permeability of 5 cfm.

(3) Manufacture of Ultraviolet Protection Patch

A support member, the first shape-retaining layer, and the ultraviolet protection layer-forming member were disposed to be sequentially stacked and then were laminated at a temperature of 80° C. through simplified lamination at a temperature to plasticize the hydrophobic resin of the ultraviolet protection layer-forming member, thereby manufacturing an ultraviolet protection patch including a non-porous ultraviolet protection layer formed by forming the ultraviolet protection layer-forming member into a film. The ultraviolet protection layer provided in the manufactured ultraviolet protection patch had a thickness of 4 μm and a basis weight was 8 g/m².

Examples 19 to 36

Ultraviolet protection patches as shown in Tables 4 to 6 below were manufactured in the same manner as in Example 1 except that a content of an ultraviolet protection agent, a thickness and a basis weight of a first shape-retaining layer and a second shape-retaining layer, a basis weight of an ultraviolet protection layer, and the like were changed Experimental Example 2

The following items were measured on the ultraviolet protection patches prepared according to Examples 18 to 36, and the measured results are shown in Tables 4 to 6 below
1. Measurement of Ultraviolet Protection Factor (UPF)

A UPF, UV-A transmittance (315 nm to 400 nm), and UV-B transmittance (290 nm to 315 nm) were measured on the ultraviolet protection patches according to Examples 18 to 36 under a condition of a wavelength interval of 5 nm through an ultraviolet-visible-near-infrared spectrophotometer (UV-VIS-NIR spectrophotometer, Perkin Elmer Lambda 1050).
2. Evaluation of Visibility of Adherend The ultraviolet protection patches according to Examples 18 to 26 were attached to skin, and visibility of an adhered was evaluated on 30 workers with over ten years' experience in the related industry (1—very bad, 2—bad, 3—slightly bad, 4—medium, 5—slightly good, 6—good, and 7—very good).
3. Evaluation of Adhesion and Elasticity Stiffness (tearing) was evaluated on the ultraviolet protection patches according to Examples 18 to 26, the ultraviolet protection patches were attached to skin, and elasticity (inhibition of movement of an adherend) was comprehensively evaluated on 30 workers with over ten years' experience in the related industry (1—very bad, 2—bad, 3—slightly bad, 4—medium, 5—slightly good, 6—good, and 7—very good).

TABLE 4

| Classification | | Example 18 | Example 19 | Example 20 | Example 21 | Example 22 | Example 23 |
|---|---|---|---|---|---|---|---|
| First shape-retaining layer | Thickness (μm) | 15 | 1 | 3 | 30 | 40 | 15 |
| | Basis weight (g/m²) | 15 | 15 | 15 | 15 | 15 | 1 |
| Ultraviolet protection layer | Content of ultraviolet protection agent (parts by weight) | 55 | 55 | 55 | 55 | 55 | 55 |
| | Type of ultraviolet protection agent | Organic and inorganic mixture | Organic and inorganic mixture | Organic and inorganic mixture | Organic and inorganic mixture | Organic and inorganic mixture | Organic and inorganic mixture |
| | Basis weight (g/m²) | 8 | 8 | 8 | 8 | 8 | 8 |
| Basis weight ratio of first shape-retaining layer to ultraviolet protection layer | | 1:0.53 | 1:0.53 | 1:0.53 | 1:0.53 | 1:0.53 | 1:8 |
| UPF | | 50 or more | 50 or more | 50 or more | 50 or more | 50 or more | 50 or more |
| UV-A transmittance (%) | | 2.2 | 2.8 | 2.2 | 2.1 | 2.7 | 2.6 |
| UV-B transmittance (%) | | 0.1 | 0.4 | 0.1 | 0.2 | 0.3 | 0.2 |
| Visibility of adherend | | 6.8 | 6.6 | 6.7 | 6.8 | 6.5 | 6.3 |
| Stiffness and elasticity | | 6.8 | 3.1 | 6.7 | 6.6 | 2.3 | 2.3 |

TABLE 5

| Classification | | Example 24 | Example 25 | Example 26 | Example 27 | Example 28 | Example 29 |
|---|---|---|---|---|---|---|---|
| First shape-retaining layer | Thickness (μm) | 15 | 15 | 15 | 15 | 15 | 15 |
| | Basis weight (g/m²) | 4 | 20 | 35 | 15 | 15 | 15 |
| Ultraviolet protection layer | Content of ultraviolet protection agent (parts by weight) | 55 | 55 | 55 | 3 | 10 | 100 |
| | Type of ultraviolet protection agent | Organic and inorganic mixture | Organic and inorganic mixture | Organic and inorganic mixture | Organic and inorganic mixture | Organic and inorganic mixture | Organic and inorganic mixture |
| | Basis weight (g/m²) | 8 | 10 | 8 | 8 | 8 | 8 |
| Basis weight ratio of first shape-retaining layer to ultraviolet protection layer | | 1:2 | 1:0.5 | 1:0.23 | 1:0.53 | 1:0.53 | 1:0.53 |
| UPF | | 50 or more | 50 or more | 50 or more | less than 50 | 50 or more | 50 or more |
| UV-A transmittance (%) | | 2.2 | 2.3 | 2.2 | 8.3 | 2.9 | 2.4 |
| UV-B transmittance (%) | | 0.2 | 0.2 | 0.2 | 2.1 | 0.4 | 0.3 |
| Visibility of adherend | | 6.6 | 6.8 | 6.4 | 6.4 | 6.6 | 6.6 |
| Stiffness and elasticity | | 6.8 | 6.7 | 1.9 | 6.7 | 6.5 | 6.6 |

TABLE 6

| Classification | | Example 30 | Example 31 | Example 32 | Example 33 | Example 34 | Example 35 | Example 36 |
|---|---|---|---|---|---|---|---|---|
| First shape-retaining layer | Thickness (μm) | 15 | 15 | 15 | 15 | 10 | 15 | 15 |
| | Basis weight (g/m²) | 15 | 15 | 5 | 15 | 10 | 15 | 15 |
| Ultraviolet protection layer | Content of ultraviolet protection agent (parts by weight) | 130 | 55 | 55 | 55 | 55 | 10 | 10 |

TABLE 6-continued

| Classification | Example 30 | Example 31 | Example 32 | Example 33 | Example 34 | Example 35 | Example 36 |
|---|---|---|---|---|---|---|---|
| Type of ultraviolet protection agent | Organic and inorganic mixture | Organic and inorganic mixture | Organic and inorganic mixture | Organic and inorganic mixture | Organic and inorganic mixture | Only organic agent | Only inorganic agent |
| Basis weight (g/m$^2$) | 8 | 0.5 | 4 | 20 | 30 | 4 | 8 |
| Basis weight ratio of first shape-retaining layer to ultraviole protection layer | 1:0.53 | 1:0.03 | 1:0.8 | 1:1.33 | 1:3 | 1:0.53 | 1:0.53 |
| UPF | 50 or more | less than 50 | 50 or more | 550 or more | 50 or more | less than 50 | less than 50 |
| UV-A transmittance (%) | 2.3 | 10.4 | 4.3 | 2.0 | 2.1 | 6.7 | 5.9 |
| UV-B transmittance (%) | 0.1 | 3.2 | 0.7 | 0.1 | 0.1 | 1.8 | 1.9 |
| Visibility of adherend | 2.9 | 6.8 | 6.7 | 6.6 | 3.6 | 6.6 | 6.7 |
| Stiffness and elasticity | 5.7 | 6.8 | 6.6 | 6.8 | 2.8 | 6.7 | 6.7 |

As can be seen from Tables 4 to 6, in Examples 18, 20, 21, 24, 25, 28, 29, 32, and 33, which satisfy all of a content of the ultraviolet protection agent, a thickness and basis weight of the first shape-retaining layer and the second shape-retaining layer, and a basis weight of the ultraviolet protection layer according to the present invention, it can be confirmed through an effect of the excellent visibility of the adherend and an effect of the excellent adhesion and elasticity that effects, in which movement of the adherend is not inhibited even on an uneven surface of the adherend, the UPF is high, the UV-A transmittance and the UV-B transmittance are low, and the stiffness is excellent, are all exhibited at the same time as compared with Examples 9, 22, 23, 26, 27, 30, 31, and 34 to 36 which do not satisfy any one among these.

While the embodiments of the present invention have been described above, the present invention is not limited to the embodiment presented herein. One skilled in the art may easily suggest other embodiments due to addition, modification, deletion, and the like of components within the scope and spirit of the present invention, and the addition, modification, deletion, and the like of the components fall within the scope and spirit of the present invention.

The invention claimed is:

1. An ultraviolet protection patch comprising:
an ultraviolet protection layer including a support component and an ultraviolet protection agent;
a first shape-retaining layer which is a fiber web provided on a first surface of the ultraviolet protection layer; and
a second shape-retaining layer which is a fiber web provided on a second surface of the ultraviolet protection layer, wherein the second surface is opposite to the first surface,
wherein the first shape-retaining layer and the second shape-retaining layer each independently have a thickness of 2 μm to 35 μm and a basis weight of 3 g/m$^2$ to 30 g/m$^2$, and a basis weight ratio of the first shape-retaining layer to the ultraviolet protection layer and a basis weight ratio of the second shape-retaining layer to the ultraviolet protection layer are each independently in a range of 1:0.3 to 1:2.5.

2. The ultraviolet protection patch of claim 1, wherein the support component includes a hydrophilic resin, and
the ultraviolet protection layer is a porous substrate formed of a plurality of first nanofibers including the hydrophilic resin and the ultraviolet protection agent.

3. The ultraviolet protection patch of claim 2, wherein the hydrophilic resin includes at least one selected from the group consisting of polyvinyl alcohol (PVA), polyvinylpyrrolidone (PVP), polyethylene oxide (PEO), carboxymethyl cellulose (CMC), a polyacrylic acid (PAA), carboxyl methyl cellulose (CMC), starch, and a hyaluronic acid.

4. The ultraviolet protection patch of claim 1, wherein the support component includes a hydrophobic resin, and
the ultraviolet protection layer is a non-porous substrate including the hydrophobic resin and the ultraviolet protection agent.

5. The ultraviolet protection patch of claim 4, wherein the hydrophobic resin includes at least one selected from the group consisting of thermoplastic polyurethane resin (TPU), polyacrylonitrile, polyethylene, polypropylene, polystyrene, polyvinylidene fluoride, and polymethyl methacrylate.

6. The ultraviolet protection patch of claim 1, wherein the ultraviolet protection layer includes the ultraviolet protection agent in a content of 5 to 110 parts by weight with respect to 100 parts by weight of the support component.

7. The ultraviolet protection patch of claim 1, wherein the ultraviolet protection agent includes both an organic ultraviolet protection agent and an inorganic ultraviolet protection agent.

8. The ultraviolet protection patch of claim 1, wherein the first shape-retaining layer and the second shape-retaining layer are each independently a fiber web formed of a plurality of second nanofibers.

9. The ultraviolet protection patch of claim 1, wherein the first shape-retaining layer and the second shape-retaining layer are each independently made of a mixture resin which includes an elastic resin including at least one selected from the group consisting of thermoplastic polyurethane resin (TPU), polymethyl methacrylate (PMMA), and polypyrrole (PPy) and a strength reinforcing resin including at least one selected from the group consisting of polyvinylidene fluoride (PVDF), polystyrene (PS), and polyethersulfone (PES).

10. The ultraviolet protection patch of claim 9, wherein the mixture resin includes the elastic resin and the strength reinforcing resin in a weight ratio of 1:0.2 to 1:4.

11. The ultraviolet protection patch of claim 1, further comprising a support member provided on one surface of the first shape-retaining layer.

12. A method of applying an ultraviolet protection patch, the method comprising:
performing moisture treatment on at least a portion of the ultraviolet protection patch according to claim 1 to dissolve the ultraviolet protection layer and fill at least some pores of the first shape-retaining layer and the second shape-retaining layer; and attaching the ultraviolet protection patch to skin.

* * * * *